(12) United States Patent
Ziouzenkova

(10) Patent No.: US 8,858,990 B2
(45) Date of Patent: Oct. 14, 2014

(54) CAPSULE OF THERMOGENIC CELLS FOR TREATING A METABOLIC DISEASE

(75) Inventor: Ouliana Ziouzenkova, Columbus, OH (US)

(73) Assignee: The Ohio State University, Columbus, OH (US)

( * ) Notice: Subject to any disclaimer, the term of this patent is extended or adjusted under 35 U.S.C. 154(b) by 132 days.

(21) Appl. No.: 12/884,587

(22) Filed: Sep. 17, 2010

(65) Prior Publication Data

US 2011/0064797 A1 Mar. 17, 2011

Related U.S. Application Data

(60) Provisional application No. 61/243,367, filed on Sep. 17, 2009.

(51) Int. Cl.
| | |
|---|---|
| A61K 9/48 | (2006.01) |
| A01N 63/00 | (2006.01) |
| A61K 48/00 | (2006.01) |
| C12N 15/00 | (2006.01) |
| C12N 5/077 | (2010.01) |
| A61K 9/50 | (2006.01) |
| C12N 5/0775 | (2010.01) |
| A61K 9/00 | (2006.01) |
| C07K 14/245 | (2006.01) |
| A61K 35/12 | (2006.01) |

(52) U.S. Cl.
CPC ........... *A61K 9/0024* (2013.01); *C12N 2510/00* (2013.01); *C12N 5/0653* (2013.01); *A61K 9/5031* (2013.01); *C12N 5/0667* (2013.01); *C12N 2533/74* (2013.01); *C12N 2533/32* (2013.01); *A61K 9/5036* (2013.01); *C12N 2501/70* (2013.01); *C07K 14/245* (2013.01); *A61K 2035/126* (2013.01)
USPC .......................... 424/451; 424/93.21; 435/455

(58) Field of Classification Search
None
See application file for complete search history.

(56) References Cited

U.S. PATENT DOCUMENTS

| | | | | |
|---|---|---|---|---|
| 4,391,909 A | * | 7/1983 | Lim ................................ | 435/1.1 |
| 6,960,351 B2 | | 11/2005 | Dionne et al. | |
| 7,427,415 B2 | | 9/2008 | Scharp et al. | |
| 2003/0212016 A1 | | 11/2003 | Gimeno et al. | |
| 2003/0229204 A1 | | 12/2003 | Spiegelman et al. | |
| 2010/0150885 A1 | * | 6/2010 | Tseng et al. ................ | 424/93.21 |

FOREIGN PATENT DOCUMENTS

WO 03004613 A2 1/2003

OTHER PUBLICATIONS

Gharapetian, et al. (1987) "Polyacrylate Microcapsules for Cell Encapsulation: Effects of Copolymer Structure on Membrane Properties", 30(6): 775-79.*
Tseng, et al. (as evidenced by Kiefer, et al. (2012) "Retinaldehyde dehydrogenase 1 regulates a thermogenic program in white adipose tissue", Nature Medicine: 18: 918-25(Text version supplied, due to 12 month delay in availability of PDF: 34 pages long)).*
Welsh, et al. (1997) "Reporter gene expression for monitoring gene transfer", Current Opinion in Biotechnology, 8: 617-622.*
http://en.wikipedia.org/?title=Ob/ob_mouse, "ob/ob mouse", Wikipedia online encyclopedia, no author, journal, volume, issue, or page numbers provided (2 pages long). downloaded Nov. 16, 2013.*
http://en.wikipedia.org/wiki/Basal_metabolic_rate "Basal Metabolic Rate", Wikipedia online encyclopedia, no author, journal, volume, issue, or page numbers provided (1 page long). downloaded Nov. 16, 2013.*
Pankov (2010) Biomed. Kim. 56(2): 152-67 (Abstract Only).*
International Searching Authority, International Search Report and Written Opinion in corresponding PCT Application No. PCT/US2010/049300, mailed Dec. 7, 2010 (9 pages).
Kajimura, Shingo, et al, Initiation of myoblast/brown fat switch through a PRDM16-C/EBP-β transcriptional complex, Nature, Aug. 27, 2007, 460(7259), 1154-1158 (13 pages).

* cited by examiner

*Primary Examiner* — Robert M Kelly
(74) *Attorney, Agent, or Firm* — MacMillan, Sobanski & Todd, LLC

(57) ABSTRACT

Described herein are methods and devices for treating a metabolic disease that involve implanting a micro-device into a tissue of a subject having a metabolic disease. The micro-device includes a plurality of thermogenic cells encapsulated in a biocompatible capsule. The capsule includes a core to accommodate the plurality of thermogenic cells and a porous immunoprotective membrane that allows for metabolic interaction between the plurality of thermogenic cells and the tissue.

7 Claims, 8 Drawing Sheets

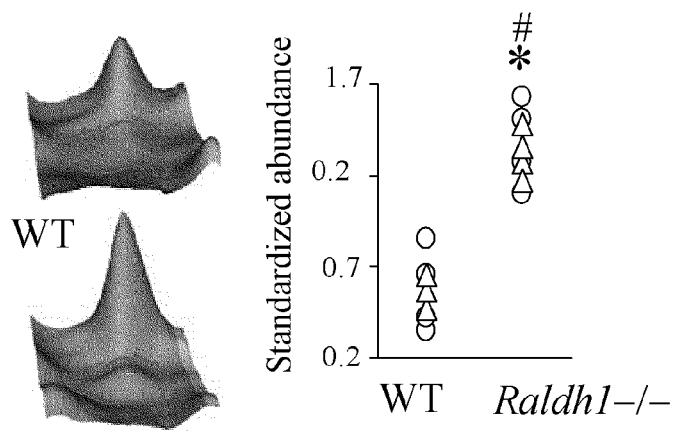
FIG. 2A Raldh1−/−
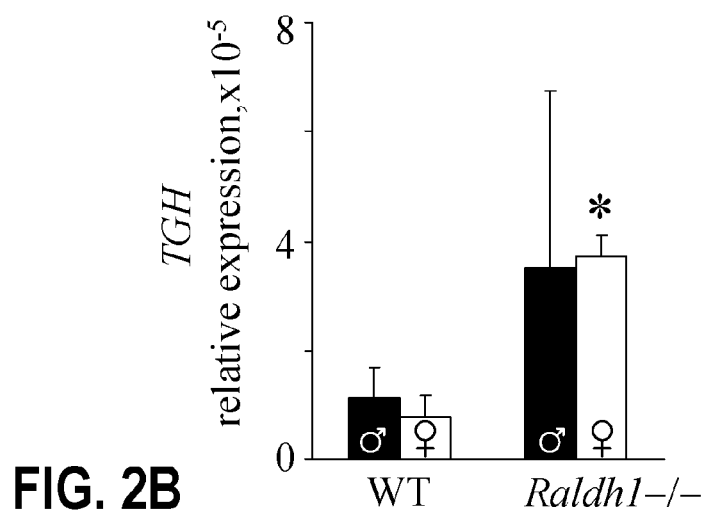
FIG. 2B
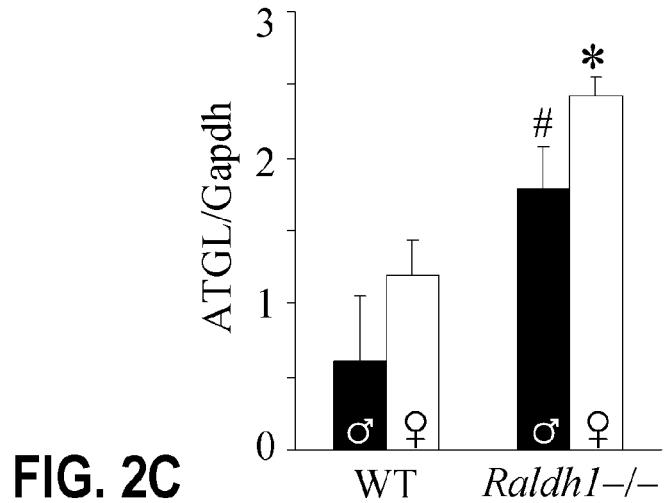
FIG. 2C

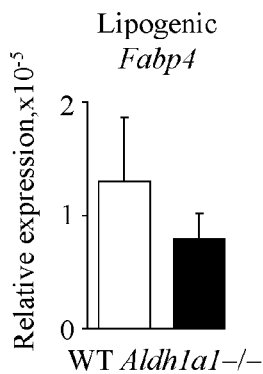
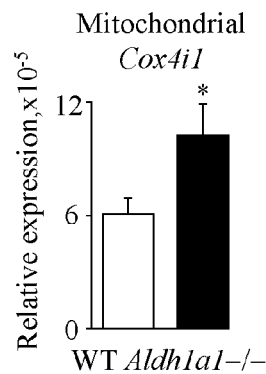
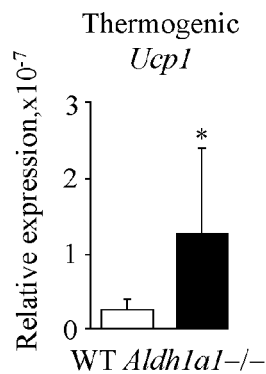
FIG. 3A     FIG. 3B     FIG. 3C
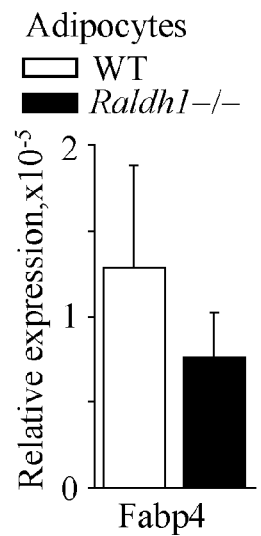
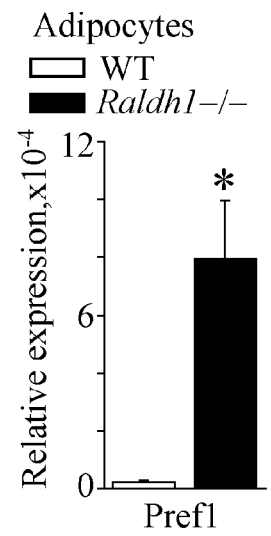
FIG. 4A     FIG. 4B
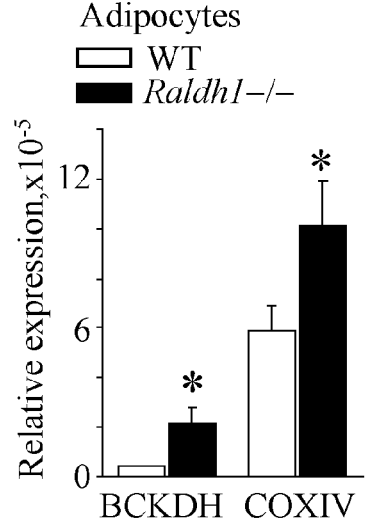
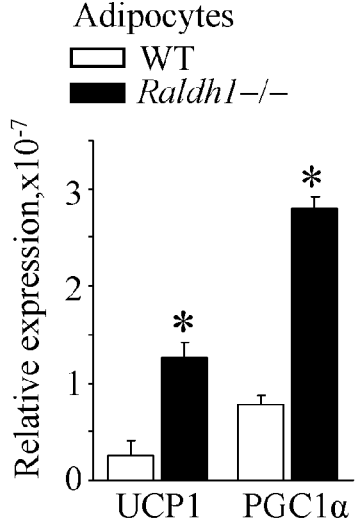
FIG. 4C     FIG. 4D

CAPSULE OF THERMOGENIC CELLS FOR TREATING A METABOLIC DISEASE

CROSS REFERENCE TO RELATED APPLICATIONS

This application claims the benefit of U.S. Provisional Application Ser. No. 61/243,367, filed on Sep. 17, 2009, the disclosure of which is expressly incorporated by reference herein in its entirety.

FIELD

The invention relates generally to devices and methods for treating a metabolic disease and, more particularly, relates to a capsule containing cells having a therapeutic benefit for the treatment of a metabolic disease and associated methods of use.

BACKGROUND

Visceral obesity markedly increases all-cause mortality by posing risks for the development of degenerative and inflammatory diseases, such as type 2 diabetes, cardiovascular disease, and some cancers. The annual U.S. obesity-attributable medical expenditures were estimated at $75 billion in 2003. These costs will continue to rise if obesity is not successfully treated.

Obesity is a complex psychosomatic disorder, which depends on a person's lifestyle and basal metabolism. Obesity results from energy consumption being greater than energy expenditure. The excess calories are converted to triglycerides, which are stored in unilocular white adipocyte in white adipose tissue. The predisposition to obesity is rooted in an efficient, thrifty metabolism, which prefers fat storage over energy expenditure.

Abdominal obesity is associated with enlarged fat depots around vital organs, known as visceral or omental fat, which produces a large amount of inflammatory cytokines. These cytokines provoke insulin resistance and chronic inflammation, two conditions influencing a variety of degenerative diseases including cancer, osteoporosis, type 2 diabetes, and cardiovascular diseases, as well as inflammatory responses in autoimmune diseases (including lupus). These pathologies lead to morbidity, disabilities, and mortality, raising the costs for medical treatment. For example, abdominal obesity increases risk of premature death from all causes, cancer and cardiovascular diseases from 50 to 100%. Successfully treating visceral obesity should help decrease the morbidity and mortality associated with these diseases. Correspondingly, a successful visceral obesity treatment will also decrease the healthcare costs associated with these diseases.

Obesity is typically treated by encouraging a change in lifestyle which can be supplemented by surgical intervention and pharmacological treatments. Although lifestyle changes can effectively lower adipose mass, patients often do not comply over the long term resulting weight regain. Moreover, change in lifestyles does not specifically reduce the visceral obesity that increases patients' risks for development of cancers and other degenerative disorders.

The harmful effects of visceral obesity may be mitigated in part by reducing white adipose tissue, including abdominal visceral fat. A majority of adipocytes in white fat tissue are lipogenic adipocytes which generate and store large amounts of lipids and have a unilocular appearance. White fat tissue also contains rare interspersed thermogenic adipocytes that have many mitochondria and produce heat utilizing stored lipids. In contrast to lipogenic adipocytes, thermogenic adipocytes burn fat to produce heat instead of storing it. Additionally, thermogenic adipocytes have a multilocular appearance due to the increased lipolysis releasing the esterified fatty acids used for heat production.

In rodents and other small mammals, thermogenic adipocytes are localized in brown fat, a specific organ maintaining body temperature. In humans, brown fat is transiently present in childhood. In adult humans, body temperature is maintained by interspersed thermogenic adipocytes, perivascular brown adipocytes, and muscle activity.

Increasing the proportion of thermogenic versus lipogenic adipocytes in white adipose tissue is associated with the reduced fat accumulation, decreased inflammation, and improved insulin sensitivity in rodents and humans. Thermogenic adipocytes have increased basal metabolic energy expenditure fueled by increased lipid consumption. Although thermogenic adipocytes offer an effective protection against obesity it is difficult to therapeutically increase the number of thermogenic adipocytes in humans.

The number of thermogenic adipocytes in white fat depends on genetic and environmental factors. Cold exposure and activation of $\beta$-adrenergic receptors stimulate conversion of lipogenic adipocytes into thermogenic adipocytes. This conversion leads to weight loss and improvement of metabolic parameters in human and animals. However, current pharmacological treatments targeting $\beta$-adrenergic receptors are associated with cardiovascular side effects and, as such, are not a suitable for obesity therapies.

Several genes and signaling pathways have been implicated either in the regulation of thermogenesis or in increasing the numbers of thermogenic adipocyte numbers in white fat. For example, thermogenesis is mediated by a family of mitochondrial uncoupling proteins (UCP1-5), which dissipate the proton gradient in mitochondria before it can be used to provide the energy for ATP synthesis. Among these proteins, UCP1 plays a pivotal role in energy uncoupling and is expressed in thermogenic adipocytes in abundance. Overexpression of UCP1 in white fat tissue reduces adiposity, improves glucose tolerance, and decreases food intake in both diet-induced and genetically obese mouse models.

Signaling pathways regulate cumulative effects resulting in an increased number of thermogenic adipocytes. For example, insulin signaling depends on the activity of mammalian target of rapamycin (mTOR kinase) complex and phosphorylation of its immediate target p70S6. Genetic deficiency in both raptor, a protein in the mTOR kinase complex, and p70S6 increases the number of thermogenic adipocytes in white fat. In animal models of obesity, changes in the activity of these genes in fat tissue were associated with the resistance to high-fat diet-induced obesity, insulin resistance, and chronic inflammation. Additionally, the thermogenic potential of adipocytes depends on activation of the transcriptional factor PPAR$\gamma$, a key transcriptional regulator of adipogenesis, and its co-activator PGC1$\alpha$, CCAAT/Enhancer-binding Proteins (C/EBP $\beta$) and PR domain containing 16 (PRDM16). Overexpression of these genes in lipogenic adipocytes increases biogenesis of mitochondria, UCP1 expression, and the overall thermogenic potential of adipocytes.

Vitamin A metabolism regulates these 'high-low' energy expenditure gene programs of adipocytes. Vitamin A metabolism proceeds in two enzymatic steps: 1) alcohol dehydrogenase family of enzymes oxidizes vitamin A to retinaldehyde; and then 2) retinaldehyde is oxidized to retinoic acid by retinaldehyde dehydrogenase family of enzymes (Aldh1 also referred to as Raldh). Retinoic acid regulates transcriptional activity of multiple nuclear receptors, whereas retinaldehyde inhibits transcriptional responses of a key transcriptional regulator of adipocyte differentiation, PPARγ. Deficiency in one Aldh1 enzyme, Aldh1A1, increases retinaldehyde levels in adipose tissue and prevents obesity and insulin resistance in Aldh1A1$^{-/-}$ mice on a high-fat diet. This resistance is associated with increased body temperature, UCP1 expression, and number of thermogenic cells.

While these genes and signaling pathways regulate the thermogenic potential of adipocytes, safe treatments that take advantage of these pathways are not yet available. A potential treatment to take advantage of these pathways involves genetic manipulation of adipocytes to increase their thermogenic capacity. However, gene based therapies present a long list of potential safety and regulatory concerns. Additionally, reliable gene delivery systems are not yet available and gene based treatments are extremely expensive, permanent, and run the risk of devastating side effects such as the development of cancer.

Another potential treatment involves identifying pharmaceutical compounds that increase the thermogenic capacity of adipocytes by affecting these pathways. However, developing pharmaceutical agents is also extremely expensive and can present significant safety and regulatory concerns. Moreover, systemically administered pharmaceutical agents can also have devastating side effects and may not selectively target visceral fat depots.

An additional therapeutic approach could be to manipulate the thermogenic profile of cells, such as stem cells or white adipocytes, from the subject in need of treatment for autologous transplantation back into the subject. However, this type of treatment would have to be tailored to each individual, greatly increasing the costs of treatment. Compared to stem cell therapy, transplantation of engineered cells has advantages: 1) engineered fat cells are not transformed in the body into different type of cells, 2) they generate desired effects at constant, engineered, levels. However, delivery of engineered cells for therapy in humans faces considerable obstacles. Cell implants could be rejected by the immune system. Moreover, it would be difficult to control the duration of treatment with these cells and the cells could propagate in the body.

A safe and effective treatment for obesity that increases the thermogenic capacity of adipocytes is needed. The treatment should be cost effective, safe, controllable, and available to a large population without the need for extensive tailoring to individuals. Therapies that take advantage of thermogenic genes and signaling pathways may provide a successful treatment for obesity which can, correspondingly, treat or decrease the other metabolic and inflammatory diseases associated with obesity.

SUMMARY

A treatment for obesity and associated metabolic diseases involves increasing the thermogenic capacity of the subject by implanting a device that includes a capsule and a plurality of thermogenic cells. The beneficial changes resulting from increased thermogenic capacity of a subject includes reduced fat mass, decreased inflammation, and improved insulin sensitivity. Several additional important benefits distinguish treating obesity with encapsulated engineered cells compared to other pharmacologic or stem cell-based treatments: 1) engineering fat cells exploit natural endocrine properties of fat that reduces risks of side effects, 2) fat cell properties may be designed and controlled by molecular engineering, unlike spontaneous stem cell differentiation, 3) engineered cell therapy is transient (from months to years depending on the degradation rate of the capsule), 4) engineered cells' transplantation is site-specific (fat tissue), but it can have a systemic impact through production of cytokines, 5) if desired capsules could be removed by liposuction, and 6) therapy with engineered cells in biocompatible microcapsules could be translated to humans. This therapy is expected to be cost effective and address patient-specific needs, because encapsulation permits usage of predesigned human and rodent cell lines across a large population of patients.

The thermogenic cell may be a thermogenic adipocyte or other cell type that either naturally, or as a result of engineering, has a therapeutic benefit. For example, the cell could have a desirable metabolic rate or produce a therapeutic chemical messenger, such as a cytokine, chemokine, hormone or another bioactive molecule that increases the metabolic rate in the encapsulated cells and host tissues of a subject. The thermogenic cell is encapsulated in a capsule that allows for the exchange of nutrients and chemical messengers while at the same time protects the cells from detection by the subject's immune system. The capsule is selected for its permeability to nutrients and chemical messengers, tissue response to capsules' material and its biodegradation rate. The capsule/microdevice is implanted in the subject to treat obesity and associated metabolic diseases. The capsule can be implanted into specific tissue sites, such as in specific fat depots. The treatment ends upon the degradation or removal of the capsule, such as by liposuction.

BRIEF DESCRIPTION OF THE DRAWINGS

FIG. 2A are graphs illustrating triacylglycerol lipase/hydrolase (TGH) protein levels in Aldh1A1$^{-/-}$ and wild-type mice.

FIG. 2B is a graph illustrating mRNA expression of TGH and adipose triglyceride lipase protein levels in Aldh1A1$^{-/-}$ and wild-type mice.

FIG. 2C is a graph illustrating adipose triglyceride lipase protein levels in Aldh1A1$^{-/-}$ and wild-type mice.

FIG. 3A is a graph demonstrating differential expression of lipogenic and thermogenic genes in Aldh1A1$^{-/-}$ and wild-type adipocytes.

FIG. 3B is a graph demonstrating differential expression of lipogenic and thermogenic genes in Aldh1A1$^{-/-}$ and wild-type adipocytes.

FIG. 3C is a graph demonstrating differential expression of lipogenic and thermogenic genes in Aldh1A1$^{-/-}$ and wild-type adipocytes.

FIG. 4A are graphs demonstrating differential expression of mitochondrial genes in Aldh1A1$^{-/-}$ and wild-type adipocytes.

FIG. 4B are graphs demonstrating differential expression of mitochondrial genes in Aldh1A1$^{-/-}$ and wild-type adipocytes.

FIG. 4C are graphs demonstrating differential expression of mitochondrial genes in Aldh1A1$^{-/-}$ and wild-type adipocytes.

FIG. 4D are graphs demonstrating differential expression of mitochondrial genes in Aldh1A1$^{-/-}$ and wild-type adipocytes.

DETAILED DESCRIPTION

Figure 1:
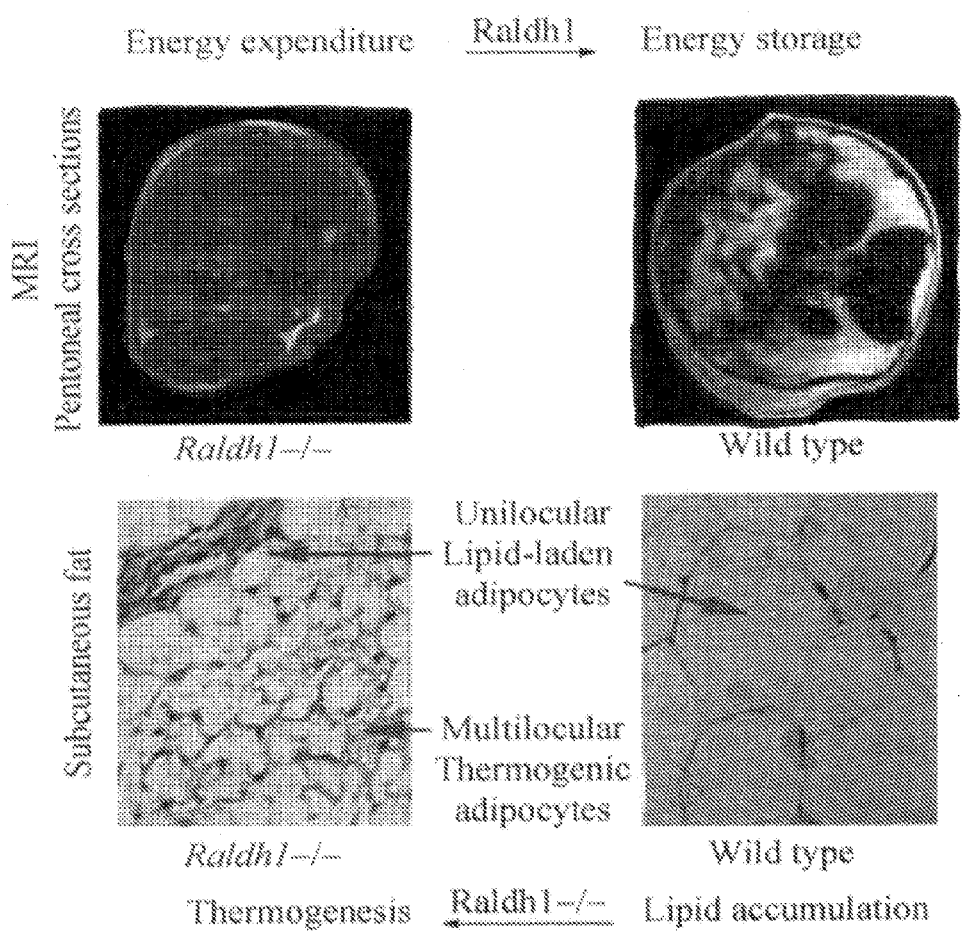
FIG. 1 are MRI images and photomicrographs showing differential accumulation of fat deposits in Aldh1A1−/− and wild-type mice.

One embodiment of the invention is directed to compositions and methods for treating a metabolic disorder in a subject such as obesity, hyperglycemia, inflammatory diseases, and cancers associated with obesity. The composition includes a micro-device configured for implantation into a tissue of a subject. The micro-device includes a plurality of thermogenic cells encapsulated in a capsule.

Thermogenic cells include cells that utilize an energy source, such as a carbohydrate or a lipid, for the purpose of producing heat. These cells have a basal metabolic rate that is greater than that of non-thermogenic cells and function as an energy sink that dissipates energy into heat instead of storing it as fat. An example of a naturally occurring thermogenic cell includes thermogenic adipocytes (also known as brown adipocytes). Thermogenic cells also include cells having a thermogenic genetic profile which can support thermogenesis and mitochondriogenesis. Molecular engineering can be used to engineer thermogenic cells from non-thermogenic cells by manipulating the expression of thermogenic genes, which include Ucp1, Pgc1a, PPAR, Prdm16, C/EBP$_\beta$, mTOR, raptor, p70S6, S6K, Aldh1, Bckdh, Cox4i1, and FOXO. Increasing the expression in engineered thermogenic cells of some thermogenic genes, such as Ucp1, Pgc1a, PPAR, Prdm16, C/EBP$_\beta$, to at least about 2-fold higher than the expression level in corresponding non-engineered cells can increase the thermogenic capacity of the engineered cells. Alternatively, decreasing the expression in engineered thermogenic cells of some of the other thermogenic genes, such as mTOR, raptor, p70S6, S6K, Aldh1, to at least about 2-fold lower activation than the level in corresponding non-engineered cells also increases the thermogenic capacity of the engineered cells. Engineered thermogenic cells can also have a mixture of increased expression of some thermogenic genes and decreased expression of other thermogenic genes. For example, a deficiency in Aldh1A1, an enzyme generating retinoic acid, leads to cumulative metabolic improvement in both diet-induced and genetically obese mouse models. Ucp1 is a major thermogenic protein expressed in thermogenic cells. In one embodiment, the engineered cells express Ucp1 at levels that are at least about 3-fold higher than the expression level in corresponding non-engineered cells. Other key genes regulating thermogenesis are raptor, p70S6, and S6K, that are components of molecular target of rapamycin (mTOR) pathway; decreasing the expression of these genes increases thermogenic potential of cells. In one embodiment, the engineered cells have about 2-fold lower activation capacity on mTOR pathway than in corresponding non-engineered cells. Additionally, the transcriptional regulators Pgc1α, Prdm16 and C/EBPβ switch differentiation of fibroblasts and muscle precursors to brown adipocytes were at least 2-fold increased in the Aldh1A1$^{-/-}$ adipocytes. All these changes in adipose tissue mitigate obesity and insulin resistance in Aldh1A1$^{-/-}$ (also referred to as Raldh1$^{-/-}$) mice on a high-fat diet by thermogenic mechanisms. Thus, genetic manipulation of non-thermogenic cells, such as preadipocytes and fibroblasts, can provide an effective way to engineer thermogenic cells in vitro. Engineered thermogenic cells may be advantageous because 1) they are not transformed in the body into different type of cells, 2) they generate desired effects at constant, engineered, levels, 3) combination of different genes could be used to increase therapeutic efficiency, and 4) combination of different type of encapsulated engineered cells could be used achieve a desired therapeutic effect.

Thermogenic cells can be engineered from isolated cells or cell lines using known molecular biology techniques. For example, thermogenic cells having decreased Aldh1A1 expression can be prepared by immortalizing embryonic fibroblasts isolated Aldh1A1$^{-/-}$ mice. Thermogenic cells can also be engineered by introducing DNA or shRNA into the cell by transfection of non-thermogenic cells such as preadipocytes and fibroblasts, such as with a lentiviral transfection procedure, to express or delete any of the desired genes, as is well known in the art. Additionally, preadipocytes may be treated with a mixture of hormones that includes thyroid hormone to stimulate thermogenic differentiation. It is contemplated that other techniques and cells may be utilized to engineer thermogenic cells.

Encapsulation of thermogenic cells, engineered or otherwise, in a capsule allows for controlling the number and function of the implanted cells and prevents their exposure to and rejection by, the subject's immune system. The capsule includes a core configured to accommodate the thermogenic cells and a porous membrane. The porous membrane can be composed of nanopolymers suitable for encapsulation, such as alginate-poly-1-lysine, which are tolerated by the subject's immune system. The capsules are tolerated by the immune system because 1) the nanopolymers are immunologically inert and 2) large immunoglobulins cannot access the capsules' contents and initiate the rejection of implanted thermogenic cells. This feature of the cells allows for the implantation of cells and cell lines originating from different individuals and even different species thereby making the micro-device available for use in a large population at a much lower cost than would be possible with autologous implantation of non-encapsulated cells. While the porous membrane prevents large immunoglobulins from accessing the contents of the core, the pore size in the polymers is sufficiently large for metabolic interaction between donor and transplanted cells that includes an influx of nutrients and cytokines, as well as an efflux of catabolic products and desirable chemical messengers.

In one embodiment, the capsule is made using the phase inversion technique. Briefly, exponentially growing recombinant cells are harvested and resuspended in a 1.5% (w/v) sterile sodium alginate solution at a density of about $10^5$ to about $2 \times 10^6$ cells/ml (Sigma). The cell suspension is then be extruded through a small gauge needle such as a 0.4-mm needle into a 100 mM $CaCl_2$ solution, using an electrostatic droplet generator, to form calcium alginate gel beads. After being gelled for about 20 mM, microbeads are then be incubated with 0.05% (w/v) poly-L-lysine (MW 20,700; Sigma) to form alginate-poly-L-lysine membrane around the surface. Alginate solution (0.15%) is then added for about 5 mM to counteract excess charges on the membranes. Lastly, the membrane-enclosed gel beads may be further suspended in 55 mM sodium citrate to liquefy the alginate gel core. Alternatively, the beads may be used with a solid core, thus avoiding the core liquification step. Microcapsules with recombinant cells are cultured in media supplemented with 10% calf serum at 37° C. in a humidified 5% $CO_2$ atmosphere for varying periods of time to assess function and viability of encapsulated cells. While the phase inversion technique is a preferable, the method described above is exemplary and variations of this method are contemplated. For example, composition of the polymer may be varied to design microcapsules with different pore sizes and periods of degradation. In addition, other methods of forming microcapsules and other types of microcapsules may be used in with this device.

Varying the composition of the polymer helps with designing microcapsules with different pore sizes and periods of degradation. These polymer properties can limit the period of treatment with the thermogenic cells and regulate the release of products from the microcapsules. Cells in a microcapsule can function from a few days to a few years. After polymer degradation compromises the integrity of the microcapsule, the thermogenic cells are recognized by the cells of the host immune system and rejected, thereby terminating the treatment. Additionally, treatments can be terminated by removing the capsules such as by liposuction or other tissue dissection methods. Tracking and removing the capsules can be aided by the inclusion of a radio microdetection device or a fluorescent molecule, such as a fluorescent protein. For example, the thermogenic cells could be engineered to express the green fluorescent protein (GFP) or the capsules themselves could include a fluorescent material. The host and donor adipocyte populations can then be analyzed using laser dissection and capture microscopy. WT and thermogenic preadipocytes expressing GFP enable the usage of this technique.

One microcapsule can include a few cells to millions of cells. Cells could be either identical or contain different genes. Alternatively, a combination of capsules containing different cells could be used. In one embodiment, the capsule contains between about $10^5$ cells to about $3\times10^6$ cells. The capsules can have a volume of at least about 50 μm. The encapsulated cells in the microcapsules are implanted, such as by injection, subcutaneously or into a specific fat depot. The numbers of injected capsules can vary from few to millions of capsules. One or consecutive injections can be used to achieve therapeutic effects. The injections can localize the microcapsules within fat tissue ensuring tissue-specific effects; although cytokines produced by the encapsulated cells can also induce systemic responses.

The methods and device described herein provide new therapeutic modalities for treatment and prevention of complex metabolic disorders, (e.g. abdominal obesity, insulin resistance, and non Hodgkin lymphoma). The thermogenic cells and delivered in microcapsules have important benefits compared to another treatments, such as pharmacologic or stem cell-based: 1) thermogenic fat cells exploits the natural endocrine properties of fat tissue that pluripotent physiologic effects and low risks of side effects, 2) fat cell properties are designed and controlled by molecular engineering, e.g. gene overexpression or deletion, 3) engineered cell therapy is transient (from days to years), and could be terminated by removal such as by liposuction, 4) engineered cells' transplantation is site specific (i.e., can target specific fat depots); however, it can have a systemic impact through production of cytokines, and 5) therapy with engineered cells in biocompatible microcapsules could be translated to humans.

The methods and devices described herein provide a new therapeutic modality: treatment of degenerative and inflammatory disorders by implantation of engineered thermogenic cells delivered in nanodevices. Implantation of encapsulated thermogenic cells in adipose tissue will suppress abdominal obesity, and related to these diseases hyperglycemia, chronic inflammation, and occurrence of non-Hodgkin blood cancer. Molecular biology techniques are used to engineer thermogenic cells with increased energy expenditure and/or anti-inflammatory cytokine (such as adiponectin) production.

Engineered thermogenic lines of fat cells as described herein are useful in the therapeutic reduction of metabolic disorders including obesity, hyperglycemia, as well as many associated disorders such as haematological malignancies and inflammatory disorders, or combinations of these conditions.

The preparation of the thermogenic cell lines will be further appreciated in light of the following examples.

Example 1

Aldh1A1−/− mice resist diet-induced obesity, which develops in wild-type ("WT") mice after 6 months on a high-fat diet (45% kcal fat) (FIG. 1). Differences in protein expression in abdominal fat of Aldh1A1$^{-/-}$ and WT mice by 2-Dimensional Fluorescence Difference Gel Electrophoresis proteomic analysis were profiled (FIG. 2A). Significantly higher and mRNA expression of triacylglycerol hydrolase (TGH, FIG. 2 B) and protein levels of adipose triglyceride lipase (ATGL, FIG. 2C) were found in Aldh1$^{-/-}$ adipose tissue as compared to their expression in WT fat tissue. These data suggested that lipolysis of triglycerides and a high lipid efflux from abdominal fat are critical mechanisms for resistance to obesity in Aldh1$^{-/-}$ mice. These data also suggest that tissues that utilize triglycerides as an energy resource might be therapeutically beneficial in treating obesity.

Aldh1A1 deficiency also changed the expression of lipogenic (Fabp4), mitochondrial (Cox4i1) and thermogenic (Ucp1) genes in Aldh1A1$^{-/-}$ preadipocytes relative to WT preadipocytes (FIGS. 3A-3C). For this study, Aldh1a1$^{-/-}$ and WT preadipocyte cell lines were derived from embryonic fibroblasts. Preadipocytes were maintained in DMEM medium containing 10% calf serum. To induce differentiation, medium was replaced with standard differentiation medium containing 10% fetal bovine serum, 10 μg/mL insulin, 1 μM dexamethasone, 0.5 mM 3-isobutyl-1-methyl xanthine. Medium was replaced every 48 hours with DMEM containing 10 μg/mL insulin. mRNA was isolated from adipocytes after 7 days of differentiation. TaqMan analysis of mRNA expression of Fabp4 (FIG. 3A), Cox4i1 (FIG. 3B), and Ucp1 (FIG. 3C). Data are shown as a mean±SD. *, Significant differences between WT and Aldh1A1$^{-/-}$ adipocytes (P<0.05, Mann Whitney U test).

Histological examination revealed large clusters of multilocular brown like cells in the subcutaneous fat of Aldh1A1$^{-/-}$, but not of WT mice (FIG. 1). These increased numbers in thermogenic cells also were associated with other beneficial effects including improved insulin resistance, decreased circulating levels of inflammatory cytokines (Table 1) (below), and increased mineral bone density (data not shown) in Aldh1A1$^{-/-}$ compared to WT mice. In contrast, brown adipose depots were not significantly different between Aldh1A1$^{-/-}$ and WT mice (data not shown).

| | WT<br>n = 10<br>mean ± SD | Aldh1A1−/−<br>n = 9<br>mean ± SD | p<br>T-Test | Fold<br>difference<br>WT vs<br>Aldh1−/− |
|---|---|---|---|---|
| IP10 pg/mL | 66.1 ± 26.9 | 17.8 ± 5.6 | 0.0001 | 3.71 |
| INFgamma | below detection levels (68 pg/mL) in both groups | | | |
| MCP1, pg/mL | 178 ± 110 | 41.8 ± 20.2 | 0.002 | 4.26 |
| MCP3, pg/mL | 340 ± 230 | 121 ± 38 | 0.012 | 2.81 |
| MIP-1alpha, ng/mL | 0.47 ± 0.07 | 0.37 ± 0.03 | 0.0008 | 1.27 |
| MIP-1beta, pg/mL | 41.7 ± 23.6 | 33.9 ± 29.9 | n.s. | 1.23 |
| IL-1beta, ng/mL | 1.67 ± 0.2 | 1.26 ± 0.14 | 0.0001 | 1.33 |
| IL-1alpha, pg/mL | 530 ± 588 | 222 ± 201 | n.s. | 2.39 |
| CRP, mg/mL | 0.11 ± 0.04 | 0.14 ± 0.03 | n.s. | 0.79 |
| Leptin, ng/mL | 33.6 ± 9.0 | 10.8 ± 6.3 | 0.0001 | 3.11 |

Table. 1 Multi-analyte profile screening immunoassay (Rules-Based Medicine) of plasma indicates decreased inflammation Aldh1A1$^{-/-}$ vs WT mice To test whether the isolated WT and Aldh1A1$^{-/-}$ preadipocyte cultures maintain their lipogenic or thermogenic properties, WT and Aldh1A1$^{-/-}$ preadipocytes were differentiated and analyzed for expression of genetic markers of differentiation (Fabp4, a marker of differentiated lipogenic adipocytes, and Pref1, a marker of non-differentiated preadipocytes) (FIGS. 4A-4B). The expression of mitochondrial proteins Bckdh and Cox4i1 (FIG. 4C) was also measured, as well as thermogenesis markers, Ucp1 and PGC1α (FIG. 4D). FIGS. 4A-4C shows that Aldh1A1$^{-/-}$ cells expressed significantly higher levels of all mitochondrial and thermogenic markers compared to differentiated WT adipocytes. Thus, isolated Aldh1A1$^{-/-}$ cells maintain their thermogenic properties.

Together these data indicate that increased levels of thermogenic multilocular cells reduce abdominal fat by lipolysis in Aldh1A1$^{-/-}$ mice. The suppression of abdominal fat formation, consequently, decreased in chronic inflammation and increased mineral bone density. Thus, implantation of large number of thermogenic Aldh1A1$^{-/-}$ preadipocytes into adipose tissue of obese subjects should also increase basal metabolic rate and reduce weight in these obese subjects.

Example 2

Figure 5A:
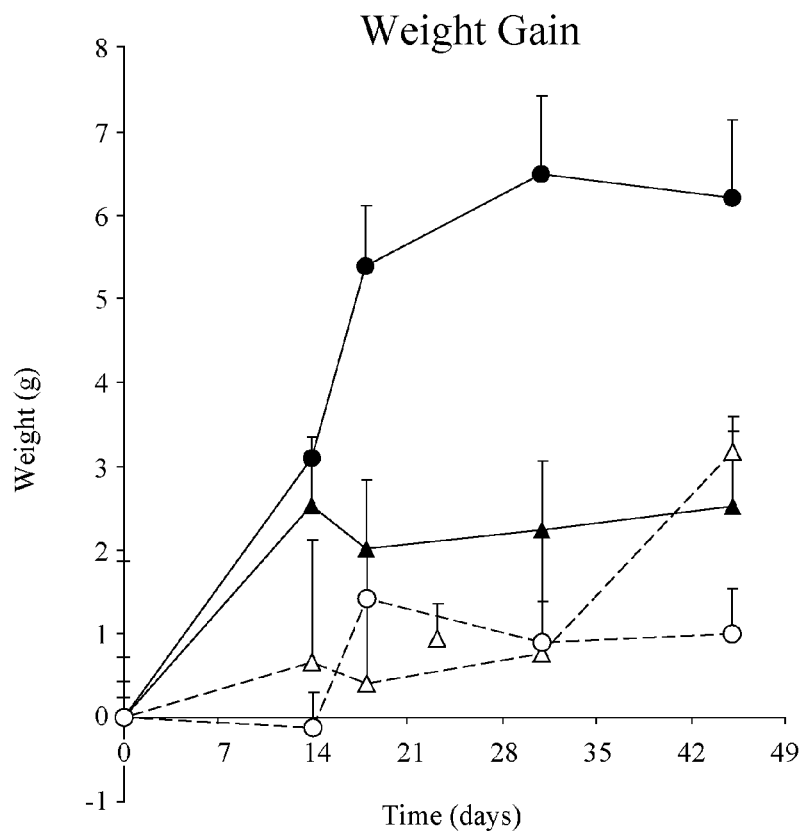
FIG. 5A is a graph demonstrating the weight change and MRI images of weight change and fat accumulation in ovarectomized WT and Aldh1A1$^{-/-}$ mice, a model of obesity in postmenopausal women.
Figure 5B:
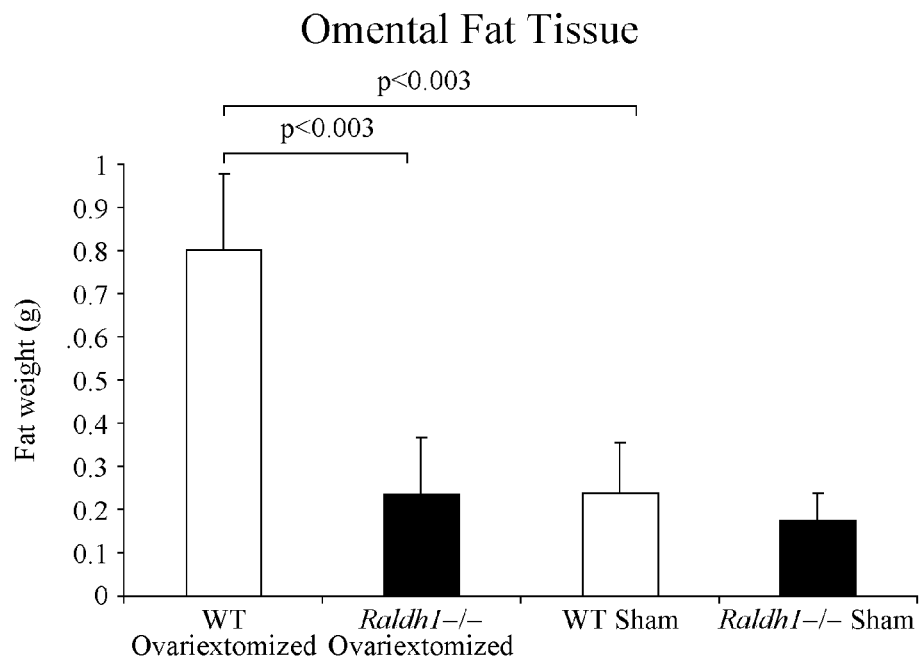
FIG. 5B is a graph demonstrating the weight change and fat accumulation in ovarectomized WT and Aldh1A1$^{-/-}$ mice.
Figure 5C:
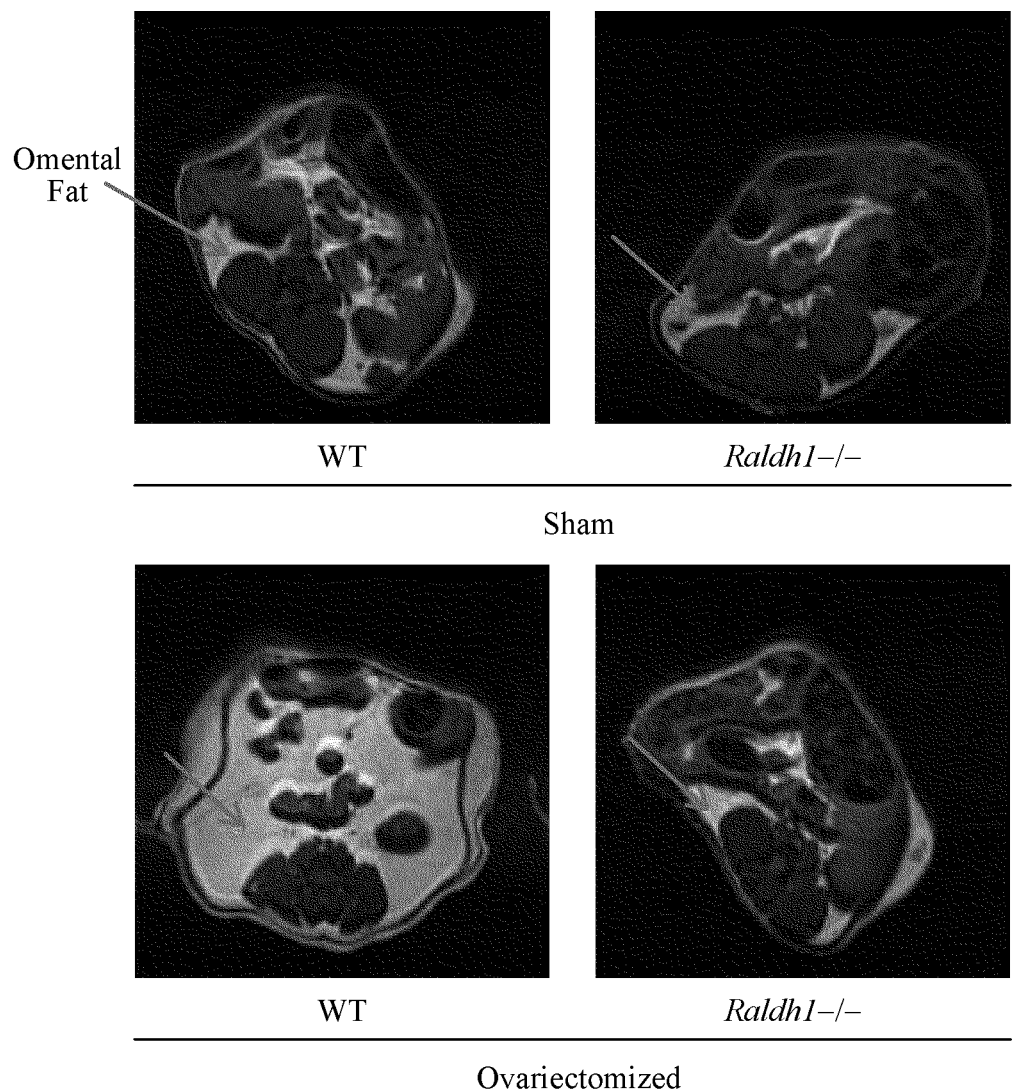
FIG. 5C are MRI images of fat accumulation in ovarectomized WT and Aldh1A1$^{-/-}$ mice.

Female Aldh1A1$^{-/-}$ mice resist obesity induced by the lack of estrogen. The ovaries were removed from female Aldh1A1$^{-/-}$ or WT (control) mice. After ovariectomy, wild type mice gain weight and acquire visceral fat even on standard chow (FIG. 5A-5C). This models mimics increase in abdominal fat in women in postmenopausal period. In contrast, ovariectomized Aldh1A1$^{-/-}$ mice resist weight gain and visceral fat accumulation. Food consumption was similar in all groups. FIG. 5A shows the weight of wild-type (WT) and Aldh1A1$^{-/-}$ mice until 45 days after surgery: WT ovariectomized (solid circles); WT Sham (open circles); Aldh1A1$^{-/-}$ (Raldh1−/−) ovariectomized solid triangles; Aldh1A1$^{-/-}$ sham (open triangles). FIG. 5B shows the weight of visceral fat pads from WT ovariectomized mice (n=4), Aldh1A1$^{-/-}$ ovariectomized mice (n=4), WT sham mice (n=5), and Aldh1A1$^{-/-}$ sham mice (n=3). T-test. FIG. 5C shows representative MRI images of each group, with large white areas of abdominal fat in ovariectomized WT females.

Example 3

Encapsulation on lipogenic (3T3-L1) and thermogenic Aldh1A1$^{-/-}$ preadipocytes were evaluated for effect on differentiation of these cells as well as for survivability under in vitro and in vivo conditions.

Figure 6A:
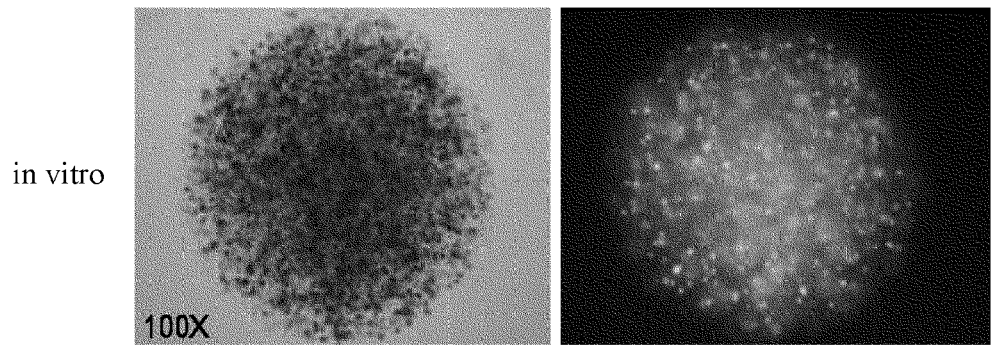
FIG. 6A are photomicrographs of encapsulated preadipocytes.
Figure 6B:
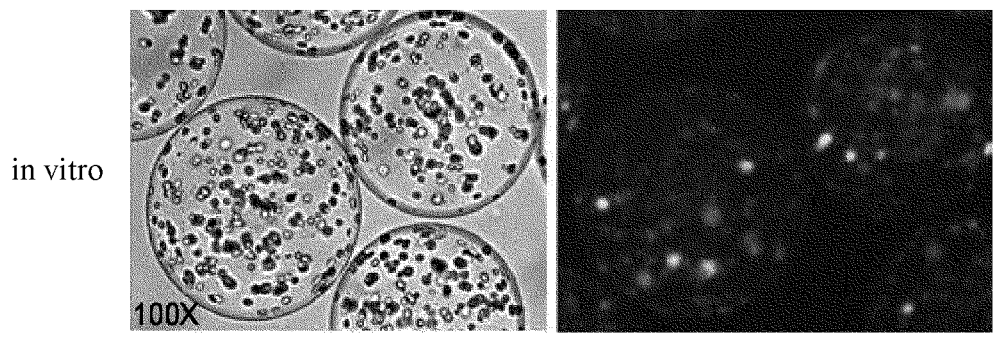
FIG. 6B are photomicrographs of encapsulated preadipocytes.
Figure 6C:
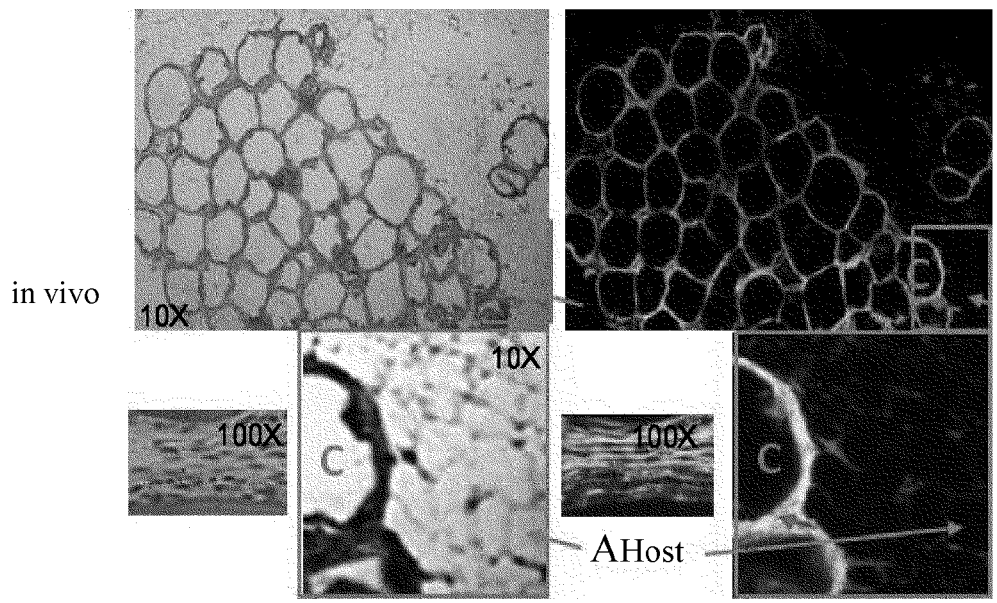
FIG. 6C are photomicrographs of encapsulated preadipocytes.

As shown in FIG. 6A-6C, WT adipocytes were transfected with lentivirus (PReceiver-Lv08GFP, Lentigen). GFP labeling allows for tracking of the transfected cells. Single transfected cells were selected to derive GFP-labeled preadipocyte cell lines (Right panels: fluorescent microscope images; Left panels: light microscope images). Similar to the non-transfected cells, encapsulated WT$^{GFP}$ adipocytes were also differentiated in vitro. These findings showed permeability of capsules for nutrients and hormones. Nonetheless, further examination of genes indicative of functional adipocytes will be examined for confirmation of adipocyte features in culture. Expression is tested of mRNA gene markers for preadipocytes (Pref1), adipocytes (PPARγ, Fabp4), subcutaneous and abdominal markers (adiponectin, vaspin), brown adipocytes (Ucp1, Ucp3), and mitochondrial marker (Cox4i1) using a customized TaqMan array (Applied Biotechnologies) as described below in the Exemplary Methods.

Cells were encapsulated as described in the Methods section below. Cell were attached to the solid alginate gel matrix or the core was liquefied using 55 mM sodium citrate (FIG. 6A, hard-, and FIG. 6B, liquid core encapsulation). Encapsulated adipocytes were maintained in culture under standard conditions for at least 1 month. FIG. 6C show liquid core capsules ($4*10^5$ in 0.5 mL PBS) that were injected into subcutaneous fat of a female WT mouse (10 month-old on a high-fat-diet (45% kcal from fat, Research Diets)) for 6 months. After 42 days subcutaneous fat was dissected. Paraffin embedded sections were stained with hematoxylin&eosin (H&E) to visualize all cells in the dissected adipose tissue (left panel). In the same slide GFP-labeling indicates implanted green encapsulated cells (right panel) that lined capsules' inside ('C', double ended arrows shows diameter of one capsule). FIG. 6C shows the larger, 40×, magnification of the same slide shows multiple engineered cells indicated by cell nuclei (arrow near 'C' arrow, border of capsule). The size of host adipocytes is smaller than size of capsules ('A', between two arrows, host adipocytes vs. 'C' capsules; Host adipocytes are visible only with H&E staining).

Figure 7A:
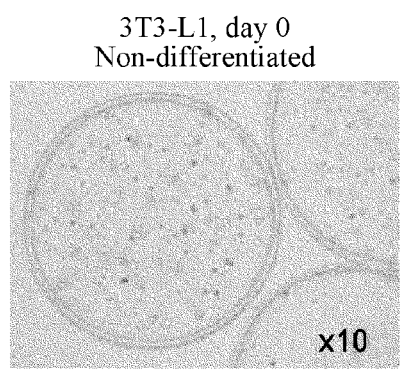
FIG. 7A are photomicrographs of differentiated encapsulated adipocytes.
Figure 7B:
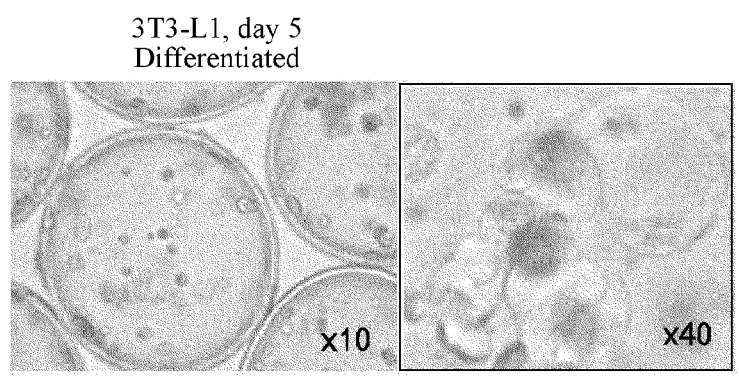
FIG. 7B are photomicrographs of differentiated encapsulated adipocytes.

To characterize different batches of capsules we developed a permeability assay using fluorescent proteins of different molecular weight (data not shown). Functional differentiation studies on encapsulated 3T3-L1 cells demonstrated that insulin and other components of standard differentiation mix diffused into capsules and induced adipogenesis seen as unilocular lipid accumulation in encapsulated cells (FIGS. 7A-7B). FIG. 7A shows non differentiated encapsulated 3T3-L1 cells. FIG. 7B shows encapsulated 3T3-L1 adipocytes were differentiated using standard protocol. Insert shows typical lipid accumulation in differentiated adipocytes.

Figure 8:
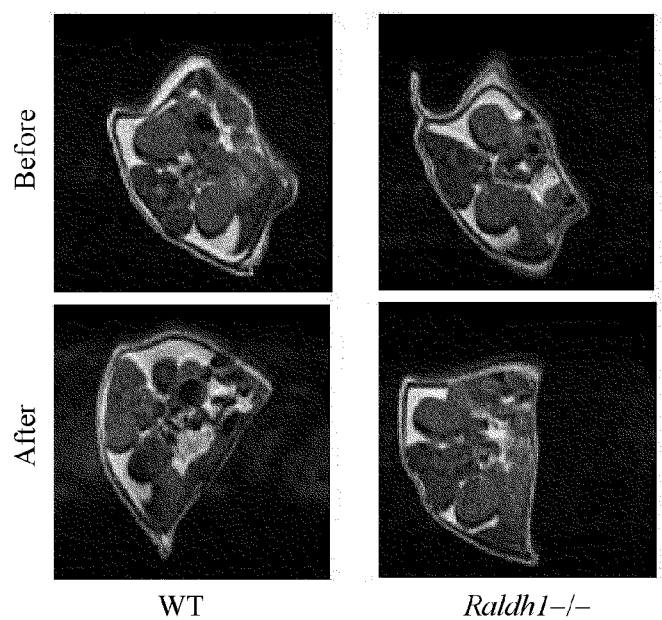
FIG. 8 are representative histological section of fat with injected capsules in mice.

The interaction between encapsulated donor adipocytes and host adipocytes was monitored and analyzed. Changes in fat amount and fat distribution induced by thermogenic cells can be, and were monitored and quantitatively analyzed by MRI (FIG. 8). To exploit thermogenic potential, WT and Aldh1A1$^{-/-}$ female mice were exposed to cold and fat accumulation was monitored before and after cold exposure. The representative images showed reduction of fat accumulation in vivo and demonstrated advantages of this in vivo imaging technique for follow up reduction of specific fat depositions.

Example 4

Figure 9:
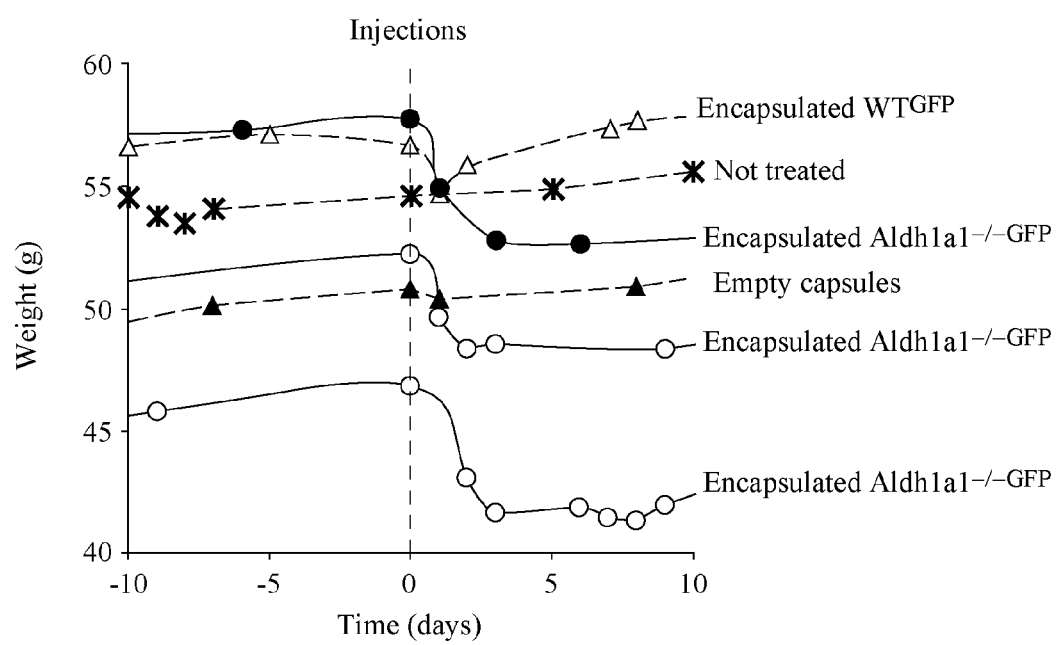
FIG. 9 are graphs representing weight loss by mice implanted with capsules containing thermogenic cells.

To test the effect of transplantation of encapsulated thermogenic cells, in this case Aldh1a1$^{-/-}$ preadipocytes, on weight gain in obese mice, obese wild type female mice (WT) were implanted with capsules containing either Aldh1A1$^{-/-}$ $_{GFP}$ preadipocytes or wild type GFP transfected (WT$^{GFP}$) preadipocytes (FIG. 9). For this study, six obese WT female mice were injected with $4\times10^5$ capsules containing no cells (empty capsules indicated with solid triangles), WT$^{GFP}$ capsules (open triangles), and AldhlA1$^{-/-GFP}$ capsules (open circle—liquid core and solid circle—solid core). One mouse was not injected (not treated). Mice weight and food consumption were monitored weekly. Injection time is indicated by the dashed line at 0 days. Food consumption (45% kcal/fat diet) was similar in all mice before and after injection, while weight was reduced only in mice injected with AldhlA1$^{-/-}$ $_{GFP}$.

Example 5

The effect of degradation of encapsulated cells on host animal tissues will be elucidated using GFP-labeled preadipocytes (WT) that are encapsulated in a polymer with a short degradation rate (one month). For these studies, encapsulated cells are injected in three groups of WT male mice. Animals are harvested at various time points, such as on day 31, 37, and 300, to assess short- and long-term effects of polymer capsule degradation. Tissues and histological examinations are performed on collected tissue to evaluate the inflammatory response and apoptosis following implant injection as compared to non-injected adipose tissue. Plasma is examined for a panel of inflammatory cytokines (see Exemplary Methods below) to evaluate systemic inflammatory response. Long-term effects (i.e. day 300) are compared in injected versus non-injected males of the same age. Histopathological analysis of all major tissues and gross phenotypic examination to identify possible side effects of treatment with engineered cells are performed by qualified pathologist.

Example 6

Although the effective concentration of microcapsules can vary widely, the optimal concentration of microcapsules in treatment of abdominal obesity can be ascertained by the following procedures.

Implantation of varying amounts of encapsulated cells (such as $10^6$; $2*10^6$; $3*10^6$; $4*10^6$; or $5*10^6$; per depot/per subject) can be performed in two groups of mice on a high-fat diet (such as, 4-5 weeks old, n=5 for WT and n=5 for Aldh1A1$^{-/-}$ microcapsules). Actual sample size for this and other studies are determined according to the equation: $n=2[(\mu_\alpha+\mu_\beta)s/\delta]$, where n, is sample size, s, standard error from the pilot study, $\delta$, difference between two groups $\mu_\alpha=1.96$ for P<0.05, $\mu_\beta=2.582$ where $\beta$ error equals 0.1. Microcapsules are injected into two subcutaneous fat depots of WT mice and animals are fed a high-fat diet (45% kcal/fat). Weight and blood glucose are measured weekly. The duration of study is determined by emerging differences in weight loss and decrease in glucose concentration in blood. Insulin resistance, fat amount, and fat distribution are examined as described in the Exemplary Methods. Mouse plasma, white, and brown fat tissue, and encapsulated cells are collected for histological and biochemical analysis. The expression of genes are studied as described in the Exemplary Methods. The green fluorescent protein-expressing Aldh1A1$^{-/-}$ and WT preadipocytes may be used. This intrinsic GFP-labeling allows for controlling the permeability of microcapsules and helps with recognition of host and donor adipocytes.

The cells can be implanted in subcutaneous or visceral depots to determine the effect of depot-specific implantation or obesity for diagnostic purposes.

Example 7

Therapeutic efficacy of different engineered fat cell lines may be compared for to identify the most effective cell lines for treating obesity as described above or for the treatment of other metabolic disease like hyperglycemia, in addition to other diseases associated with obesity such as chronic inflammation, and occurrence of non-Hodgkin lymphoma. For these studies, the thermogenic potential and therapeutic efficacy of several engineered adipocyte lines is compared. Several adipocyte lines are generated. The most efficient engineered cell lines are tested in various animal models of disease for their therapeutic efficacy. The methods and devices described herein result in an efficacious therapy for treatment of degenerative disorders in mice, and, prospectively, in humans.

As discussed above, several signaling pathways have been proposed to improve metabolic responses through increased formation of thermogenic cells. However, some of these genes are implicated in other disease processes. Whereas UCP1 dissipates energy in the existing mitochondria, overexpression of PGC1α increases mitochondrial biogenesis. The regulating mTOR pathway plays an important role in thermogenesis. However, this pathway also has been implicated in carcinogenesis. Obesity poses a high risk for development of various cancers including non-Hodgkins lymphoma ("NHL"). Mechanisms by which obesity influences NHL are not completely understood, but mTOR inhibitors are currently used for treatment of aggressive NHL. Engineered cells deficient in raptor or p70S6, two kinases in mTOR pathway, could influence metabolic parameters, and may delay the onset of lymphoma. Thus, it is important to evaluate therapeutic potential of several engineered adipocyte lines and pharmacologic efficacy for various diseases. All of these genes identified above regulate thermogenic potential of adipocytes, insulin signaling, and adipokine production in a unique way. Several adipocyte lines may be generated that: a) overexpress UCP1 or adiponectin, and/or b) are genetically deficient in raptor or p70S6 kinases. As mentioned before, these genes have been implicated in regulation of thermogenic potential of adipocytes, insulin signaling, and adipokine production. The most efficient engineered cell lines can be tested in mouse models of obesity/hyperglycemia/impaired wound healing (mLeprdb), obesity/chronic inflammation/hyperlipidemia (Lepob Ldlrtm1Her), and non-Hodgkin lymphoma (CD1-Tg(Igh-HOX11)11Idd/J) for their therapeutic potential. Implantation of specific engineered cells will treat different dysfunctions, e.g. UCP1 overexpression will reduce more fat; adiponectin overexpression will reduce insulin resistance and chronic inflammation; and reduced mTOR activity will reduce fat and suppress lymphoma development.

Thus, stably transfected preadipocytes lines for microcapsules will be generated and characterized. Preadipocytes may be transfected using known techniques for example, 3T3-L1 preadipocyte can be transfected using lentiviral constructs (pReceiver-Lv08 GFP tagged expression vector (GeneCopoeia)) containing ORF clones of gene of interests or their shRNA as described. Single GFP-positive clones are expanded and cell lines are derived from transfected clones exerting increased thermogenic activity and/or adiponectin. 3T3-L1-based cell lines may be derived that contain: 1) pReceiver-Lv08, control; 2) same vector (also in all other lines) overexpressing UCP1 (UCP1$^{+/+}$); 3) overexpressing PGC1α (PGC1α$^{+/+}$); 5) same vector containing raptor shRNA to produce raptor-deficient preadipocytes (Raptor$^{-/-}$), and 6) p70S6 deficient preadipocytes (p70S6$^{-/-}$). The expression or deficiency of the gene of interest may be verified by using standard techniques. Gene expression may also be examined after inducing adipogenesis in the transfected cell using a custom TaqMan array.

The therapeutic effects of encapsulated control, Aldh1A1$^{-/-}$, Ucp1$^{+/+}$, Pgc1α$^{+/+}$, and preadipocytes are compared in mouse models of disease, such as, of obesity/hyperglycemia/impaired wound healing. Mice that have a genetic predisposition to obesity/hyperglycemia/impaired wound healing are treated either with equal amounts of encapsulated preadipocytes (control, Aldh1$^{-/-}$, Ucp1$^{+/+}$, Pgc1α$^{+/+}$, and Raptor$^{-/-}$) or left untreated. Mice are injected with a single dose of encapsulated cells and the development of disease is followed by weekly measurements of glucose levels in blood and weight. After one month or the onset of differences in weight gain and insulin resistance, mice are submitted for body composition measurements. These data provide information on which encapsulated cells offer better protection against fat formation in specific fat depots, lipid accumulation in livers, insulin resistance, and mineral density of bones. After these measurements, tissues are collected and analyzed. Plasma is examined for a panel of pro-inflammatory cytokines to determine effect of treatment on chronic inflammation. This study helps identify which encapsulated cells are specifically effective in the suppression of weight loss, insulin resistance, and/or chronic inflammation. The encapsulated preadipocyte lines, which demonstrate therapeutic effect in reduction of weight loss and chronic inflammation, are further tested for their effects on the cholesterol levels.

The therapeutic effects of encapsulated control, Aldh1A1$^{-/-}$, Ucp1$^{+/+}$, Pgc1α$^{+/+}$, and Raptor$^{-/-}$ preadipocytes on obesity/chronic inflammation/hyperlipidemia are compared in mice. The therapeutic effects of encapsulated control, Aldh1A1$^{-/-}$, Raptor$^{-/-}$, and p70S6$^{-/-}$, preadipocytes are compared on survival in a mouse model for non-Hodgkin lymphoma (NHL). Mice that have genetic predisposition to non-Hodgkins lymphoma are treated with equal amounts of encapsulated preadipocytes (control, Aldh1A1$^{-/-}$, Raptor$^{-/-}$, and p70S6$^{-/-}$) or left untreated. Survival analysis is performed using a Kaplan-Meier plot. Encapsulated fat cells with inhibited mTOR pathway should delay onset of NHL. If this is the case, this study is repeated using therapeutically effective encapsulated cells. The duration of the study is determined by onset of NHL in the non-treated animals seen in MRI. Mice tissue are collected and analyzed. In addition, lymph node and spleen tissue are collected for histopathological evaluation of disease stage and gene expression analysis.

Although fat tissue markedly contributes to the adverse metabolic change in degenerative disorders, it functions in concert with other tissues. It is plausible that fat tissue can have less impact than expected, especially in the setting of genetically modified mice. If this is the case, combination treatment with encapsulated fat cells and the traditional pharmacologic approach is used. For example, for treatment of NHL or insulin resistance traditional mTOR inhibitors and metformin are used. An additive or even synergistic effect is expected from the improved functions of adipose tissue mediated by encapsulated cells and improved functions of other organs mediated by pharmaceuticals. Alternatively, cells can be engineered with multiple desirable genes or encapsulated cells can be injected into different tissues.

The following exemplary methods may be employed in various steps of practicing, making, using, or developing embodiments of the invention as described and claimed herein.

a. Cell Culture

Preadipocyes (fibroblasts) are maintained in high glucose (25 mM) DMEM supplemented with 10% calf serum and antibiotics. 3T3-L1 preadipocytes have been purchased from ATCC, Aldh1A1$^{-/-}$ and WT preadipocytes are derived from embryonic fibroblasts and characterized.

Encapsulation Procedure:

Encapsulation of preadipocytes is performed using the phase inversion technique as described previously. Briefly, exponentially growing recombinant cells are harvested and resuspended in a 1.5% (w/v) filter-sterilized sodium alginate solution at a density of 2×106 cells/ml (Sigma). The cell suspension is then be extruded through a 0.4-mm needle into a 100 mM $CaCl_2$ solution, using an electrostatic droplet generator, to form calcium alginate gel beads. After being gelled for 20 mM, microbeads are then be incubated with 0.05% (w/v) poly-L-lysine (MW 20,700; Sigma) to form alginate-poly-L-lysine membrane around the surface. Alginate solution (0.15%) is then added for 5 mM to counteract excess charges on the membranes. If a liquid core is desired, the capsules are further suspended in 55 mM sodium citrate to liquefy the alginate gel core. Capsules with recombinant cells are cultured in media supplemented with 10% CS serum at 37° C. in a humidified 5% $CO^2$ atmosphere for varying periods of time to assess function and viability of encapsulated cells.

Adipogenesis Induction:

The preadipocytes are differentiated in DMEM, containing a 1 μM dexamethasone, 10 μg/mL bovine insulin, 0.5 μM rosiglitazone, antibiotics, and 500 μM IBMX as described before [Green, H. et al. An established pre-adipose cell line and its differentiation in culture. *Cell* 3, 127-133 (1974)]. Preadipocytes are incubated during 7 days in differentiation medium without IBMX, which are changed every 2 days.

Transfections:

Lentiviral pReceiver-Lv08 GFP tagged expression vector (GeneCopoeia) containing ORF clones (Ucp1, Pgc1a or adiponectin) or containing shRNA for raptor and p70S6 are used to transfect 3T3-L1 preadipocytes according to manufacturer instructions. Preadipocyte cell lines are derived. Briefly, 3T3-L1 preadipocytes are plated at 3*10 density per well in a 6 well plate. After 18 h, medium are replaced with OptiMEM (Invitrogen) containing lentiviral stock (20 MOD and polybrane (6 μg/mL) for transfection. After 24 h of transfection, complete medium is added to the cells to replace a transfection medium. After 24 hours post transfection, puromycin (1 μg/mL) is added for 48 h to select transfected preadipocytes. Cell lines are derived from clones of single transfected cells. Gene overexpression or deletion is verified using TaqMan PCR analysis and Western blotting.

b. In Vivo Studies

Metabolic Measurements:

Metabolic cages (Ancare Corp.) and a Comprehensive Lab Animal Monitoring System (eight-chamber system, Columbus Instruments, Columbus, Ohio) are used to measure several metabolic parameters including food and water intake, oxygen consumption and carbon dioxide production in WT and Aldh1A1$^4$ acclimated to the powdered diet for 4 days prior before placement in metabolic cages. Metabolic rate is calculated according to Weir equation and expressed per g body weight. Insulin and glucose tolerance tests are performed after 16 hours of food deprivation by injecting human insulin (Humilin, Eli Lily, Indianapolis, Ind.) (ITT, 0.1 U/ml in physiologic solution 0.005 ml/g body weight) intraperitoneally or after a single administration of 25% dextrose (GTT, 0.004 mL/g body weight). Glucose is measured using Accu-Chek Advantage glucometer (Roche). Rectal temperature is measured with a monitoring thermometer (TH-5, Physitemp Thermalert, Clifton, N.J.) in mice exposed to 4 or 24° C. every 30 min for 4 hours.

Body Composition:

Fat percentage and mineral density are measured using dual-energy X-ray absorptiometry (DEXA) using the GE Lunar Corporation PIXImus2 Dexa Scanner and quality control plot to normalize measurements. Fat formation and distribution between visceral and subcutaneous depots and aorta thickness are measured as described before. Measurements is performed using the Bruker 11.7T NMR system (Bruker Instruments) with a 11.7-T Bruker magnet and a 52 mm internal diameter vertical bore (Bruker Instruments, Billerica, Mass.) (500 MHz/gradient strength of 300 gauss/cm). Fat accumulation is measured with a TI-weighted gradient-echo sequence on mice at the end of study. Twenty-five contiguous, 1-mm thick axial GRE slices spanning from the superior pole of the uppermost kidney to the caudal aspect of the mouse are obtained using a spin-echo sequence with a 256×256 matrix size (pixel size, 117×117×1,000 μm3). Data analysis is performed using Image J software downloaded from the NIH website (Image J, http://rsb.info.nih.gov/ij/)

Tissue Collection:

Blood is collected, such as by cardiac puncture through the anterior thoracic aperture. Serum or plasma containing EDTA (0.25 μm) are used for protein analysis and lipid profile. Total cholesterol, trigycerides, and non-esterified fatty acids are determined using enzymatic reactions (Wako, Japan). Visceral, inguinal, and brown fat adipose tissue as well as liver tissue are dissected, and the tissues are weighed. Tissue is used for histological, biochemical, protein, and RNA analysis.

c. Analysis

Lipid Analysis:

Triglyceride and cholesterol are measured using Wako colorimetric assays. Plasma lipids and lipoprotein distribution are performed at the Cardiovascular Specialty Laboratories, Inc. in Atlanta. These include total and lipoprotein cholesterol levels, triglyceride, and particle size distribution by NMR analysis.

Cell Isolation by Laser Microdissection and Pressure Catapulting (LMPC):

To isolate adipocytes within and outside of microcapsules, LCPC is performed as previously reported with some modifications. Briefly, 6-μm frozen sections are dehydrated in ethanol, placed twice in xylene, and air dried. At 100-μm intervals, sections are prepared. Intrinsic GFP-labeling of encapsulated cells allows control of permeability of microcapsules and help to recognize host and donor adipocytes. Laser microdissection and pressure catapulting (LMPC) are performed using a PALM MicroLaser system (PALM-Zeiss) containing a PALM MicroBeam (driven by PALM MicroBeam software), a PALM RoboStage, and, for high-throughput sample collection, a PALM RoboMover (driven by PALM RoboSoftware version 2.2). GFP positive and negative areas are cut under a ×10 ocular lens and catapulted directly into 25 μl of an RNA lysis solution (RNAqueous Micro kit, Ambion). RNA is isolated by the Qiagen RNeasy MicroIsolation kit and treated with DNase. The concentration of RNA is determined by the Ribogreen RNA Quantitation kit (Molecular Probes), and the RNA quality verified with the Agilent 2100 Bioanalyzer. Each RNA sample from laser captured adipocytes is derived from a pool of five mice.

Quantitative mRNA Analysis:

Real-time PCR (TaqMan) is performed using LightCycler 480 instrument [Roche Biosciences]. Gene expression is expressed as relative fold change to housekeeping genes (GAPDH, tata-Binding protein, 36B4, or 18S), which is verified as unaffected by treatment. PCR efficiency will be calculated for all primer sets and the LightCycler 480 software will be used to correct for PCR efficiency. Expression of 32 genes is analyzed in adipocytes using a custom PCR Array comprising of verified primers (Applied Biotechnologies). This array includes biomarkers of differentiated lipogenic adipocytes (Fabp4, PPARgamma, PPARdelta, ATGL, LPL, Glut4, SCD, TGL), preadipocytes (VDR, Pref-1), differentiated thermogenic adipocytes (Ucp1, Ucp3, CoxiV, FOXO, Pgc1a, PRDM16), cytokines (adiponectin, leptin, Rbp4, vaspin, Pai1) proinflammatory cytokines (IL6, TNFa, MCP1, MCP3, IP10) and enzymes participating in vitamin A metabolism (Aldh1A1-3, Adh1-4, Cyp26A, Cyp26B). Relative mRNA expression is determined by Δ-Ct method using 18S as the control.

Protein Analysis:

Plasma is collected. Cytokine levels in plasma are measured using Multi-analyte profile screening immunoassay (Rules-Based Medicine). Tissues are collected and homogenized in RIPA buffer (50 mM Tris-Cl pH 7.4. 150 mM NaCl. 1% NP40. 0.25% Na-deoxycholate. 1 mM PMSF). RIPA is supplemented with complete mini protease inhibitor and phosphatase inhibitor cocktails (Roche). All of the proposed antibodies are obtained from reputable suppliers and verified with control lysates. Western blots are performed as described before.

Histological Analysis:

Tissue samples (~30 μg) are fixed in 4% paraformaldehyde in 0.1M phosphate buffer. After fixation overnight at 4° C., the tissue are embedded in paraffin, sliced into 8-μm sections, and stained with hematoxylin-eosin for adipocyte size analysis. The sizes of adipocytes within 10 fields in every tissue block is quantified at 20× magnification using NIH Image software.

While the embodiments of the invention described herein have focused on encapsulating preadipocytes to treat a metabolic disease, such as obesity, one of ordinary skill in the art will appreciate that other diseases could be treated with similarly encapsulated cells having a other therapeutic benefits. For example, a cell line that produces an anticancer protein could be encapsulated and implanted in a tumor to treat the tumor. Or, a cell line that secretes a product, such as a hormone, cytokine, chemokine, growth factors, etc. could be encapsulated and implanted in a subject to treat any number of diseases. For example, diabetes and/or obesity could be treated with cells that secrete insulin and/or other products that increase metabolism and glucose uptake. Or, wounds could be treated with cells that secrete factors that promote wound healing. Moreover, aging and late stages of cancer, HIV, and other inflammatory disorders (e.g. cystic fibrosis) lead to the decrease of subcutaneous (aging) and other adipose tissue (inflammatory disorders). The progressive depletion of adipose tissue precedes consumption of other tissues (muscle). Together this disease is known as wasting syndrome or cachexia. In these conditions, capsules with lipogenic adipocytes can have a therapeutic effect and delay morbidity. In addition, the term "disease" is understood to mean any condition for which treatment might be sought, such as a syndrome, disorder, sign, symptom, injury, wound, etc.

What is claimed is:

1. A micro-device comprising:
   a.) a plurality of Aldh1A1$^{-/-}$ preadipocyte cells; and
   b.) a porous immunoprotective membrane,
wherein the porous immunoprotective membrane encapsulates the Aldh1A1$^{-/-}$ preadipocyte cells.

2. The micro-device of claim 1, further comprising at least one fluorescent composition, wherein the at least one fluorescent composition is expressed inside the preadipocyte cells.

3. The micro-device of claim 2 wherein the fluorescent composition includes a green fluorescent protein.

4. A method for ameliorating the symptoms of an obesity-induced metabolic disorder in a subject in need thereof, comprising:
   introducing the micro device of claim 1 into adipose tissue of a subject in need of amelioration of symptoms of an obesity-induced metabolic disorder, wherein the introduction of the micro device of claim 1 results in amelioration of
   the symptoms of the obesity-induced metabolic disorder in the subject.

5. The method of claim 4, wherein the obesity-induced metabolic disorder is selected from the group consisting of: chronic inflammation; poor bone density; poor basal metabolic rate; and excess body weight.

6. A method of reducing excess body weight resulting from obesity in a subject in need thereof, comprising:
   introducing the micro device of claim 1 into adipose tissue of a subject in need of reduction of excess body weight, wherein the introduction of the micro device of claim 1 results in
   reducing excess body weight resulting from obesity in the subject.

7. A method of reducing obesity-induced inflammation in a subject in need thereof, comprising:
   introducing the micro device of claim 1 into adipose tissue of a subject in need of reduction of obesity-induced inflammation, wherein the introduction of the micro device of claim 1 results in
   reducing obesity-induced inflammation in the subject.

* * * * *